United States Patent [19]

Dessau

[11] 4,413,154
[45] Nov. 1, 1983

[54] DIELS-ALDER CYCLODIMERIZATION OVER A CARBON MOLECULAR SIEVE CATALYST

[75] Inventor: Ralph M. Dessau, Edison, N.J.

[73] Assignee: Mobil Oil Corporation, New York, N.Y.

[21] Appl. No.: 424,774

[22] Filed: Sep. 27, 1982

[51] Int. Cl.³ .......................... C07C 3/035; C07C 3/10
[52] U.S. Cl. .................................... 585/366; 502/416; 585/368; 585/430; 585/510
[58] Field of Search ............... 585/361, 365, 366, 367, 585/368, 430, 510; 252/444

[56] References Cited

U.S. PATENT DOCUMENTS

| | | | |
|---|---|---|---|
| 2,974,176 | 3/1961 | Warner et al. | 585/366 |
| 3,168,581 | 2/1965 | Pruett | 585/366 |
| 3,444,253 | 5/1969 | Reimlinger et al. | 585/361 |
| 3,454,665 | 7/1969 | Cier | 585/366 |
| 3,755,386 | 8/1973 | Wilke et al. | 585/368 |
| 3,897,508 | 7/1975 | Tkatchenko | 585/361 |
| 3,917,730 | 11/1975 | Tkatchenko | 585/361 |

FOREIGN PATENT DOCUMENTS

| | | | |
|---|---|---|---|
| 2548428 | 5/1976 | Fed. Rep. of Germany | 585/366 |
| 1138126 | 12/1968 | United Kingdom | 585/366 |
| 1554942 | 10/1979 | United Kingdom | 585/366 |

*Primary Examiner*—Delbert E. Gantz
*Assistant Examiner*—A. Pal
*Attorney, Agent, or Firm*—Michael G. Gilman; Charles J. Speciale

[57] ABSTRACT

The present invention provides a process which is adapted for cyclodimerization of 1,3-butadiene to 4-vinylcyclohexene under Diels-Alder conditions in the presence of a large-pore carbon molecular sieve.

4 Claims, No Drawings

DIELS-ALDER CYCLODIMERIZATION OVER A CARBON MOLECULAR SIEVE CATALYST

BACKGROUND OF THE INVENTION

This invention relates to a catalytic process for the cyclization of alkene compounds, as exemplified by the cyclodimerization of 1,3-butadiene to 4-vinylcyclohexene.

U.S. Pat. No. 3,444,253 discloses and claims a process for the dimerization of 1,3-butadiene to produce 4-vinylcyclohexene-1 using copper(I) zeolite X, or copper(I) zeolite Y. The present invention represents an effective alternative to the process of said patent.

DESCRIPTION OF THE INVENTION

It has been found that a high Diels-Alder conversion can be obtained by utilizing a large-pore carbon molecular sieve catalyst for cyclodimerization of a conjugated alkadiene-containing feedstock.

The term "large-pore" refers to a non-crystalline carbon form of a molecular sieve having an average pore size in a range between about 8–100 angstroms.

A suitable type of molecular sieve for utilization in the invention process is exemplified by a commercial product such as Carbosphere ® (Alltech Associates). This type of spherical carbon molecular sieve has a surface area of about 1000 m²/gm, and has a pore size of about 13 angstroms. The mesh size of the carbon molecular sieve can be obtained in ranges varying between about 60–80 mesh and 120–140 mesh. The packed density of a carbon molecular sieve in the form of hard dense beads is about 0.6 g/cc.

The invention process is particularly advantageous for cyclodimerization of 1,3-butadiene. The cyclodimerization of 1,3-butadiene proceeds as follows to yield 4-vinylcyclohexene:

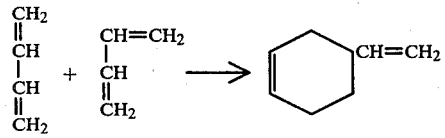

Other alkadienes which can be cyclodimerized are illustrated by isoprene, chloroprene, 1,3-pentadiene, cyclopentadiene, and the like. The cyclodimerization also can be effected between different conjugated dienes, dienes and monoalkenes, dienes and acetylenes, and the like. For example, maleic anhydride can be reacted with cyclopentadiene. Conjugated alkadienes can also be co-cyclized with alkynes such as dimethylacetylene.

An important advantage of the invention process is that high conversions are obtained with a copper-free catalyst, as opposed to the prior art methods of carrying out said reaction in the manner previously described. The invention process can be conducted in several ways, such as a continuous process or a batch process. The 1,3-butadiene dimerization, for example, can be accomplished at temperatures in the range of about room temperature to temperatures as high as 400° C. or 500° C. However, the preferred temperature range is about 150° to 300° C. The reaction preferably is conducted at a pressure between about 1–1000 psi, and the product is recovered from the reaction mixture by standard procedures such as fractional distillation or the like.

It was unexpected that a Diels-Alder reaction such as the cyclodimerization of 1,3-butadiene to 4-vinylcyclohexene could be significantly catalyzed by a molecular sieve not containing copper in the plus one valence state as has heretofore been the case with prior art zeolites (e.g., as described in U.S. Pat. No. 3,444,253).

It is an important aspect of the invention process that the cyclization product resulting from the catalyzed Diels-Alder reaction must have sufficiently small molecular dimensions to permit the diffusion of the said product out of the large-pore structure of the carbon molecular sieve catalyst.

The following Example is further illustrative of the invention process.

EXAMPLE

The cyclodimerization of 1,3-butadiene is conducted in a downflow glass reactor packed with 5–10 grams of a selected catalyst. The 1,3-butadiene flow is adjusted to about 10 cm/min. and the temperature raised to about 200°–250° C. The reaction effluent is sampled with an in-line gas chromatograph and the liquid product is collected for analysis by gas chromatograph mass spectroscopy. The results obtained are summarized in the Table.

At 200°–250° C. and atmospheric pressure, the thermal uncatalyzed conversion of 1,2-butadiene to 4-vinylcyclohexene is less than 0.1% under the flow conditions.

The major product is 4-vinylcyclohexene. A small amount of a higher boiling product, possibly cyclooctadiene-1,5, is also formed.

As indicated in the Table, a carbon molecular sieve (Run 2) in accordance with the present invention is an active catalyst for cyclodimerization of 1,3-butadiene to 4-vinylcyclohexene.

TABLE

| Conversion Of 1,3-Butadiene To 4-Vinylcyclohexene ||| 
| --- | --- | --- |
| Run | Catalyst | % Conversion |
| 1 | None | <0.1 |
| 2 | Carbon Mol Sieve | >30 |
| 3 | Silica Gel | 1 |
| 4 | Synpore | 0.8 |

What is claimed is:

1. A process for cyclodimerization of a conjugated alkadiene which comprises contacting a conjugated alkadiene-containing feedstock with a large-pore carbon molecular sieve.

2. A process in accordance with claim 1 wherein the carbon molecular sieve has an average pore size in the range between about 8–100 angstroms.

3. A process in accordance with claim 1 wherein the reaction is conducted at a temperature between about 150°–300+° C.

4. A process in accordance with claim 1 wherein the conjugated alkadiene is 1,3-butadiene, and the cyclodimerized product is 4-vinylcyclohexene.